United States Patent [19]

Kurosawa et al.

[11] Patent Number: 5,818,581
[45] Date of Patent: Oct. 6, 1998

[54] ELEMENTAL ANALYSIS METHOD AND APPARATUS

[75] Inventors: Satoru Kurosawa; Yoshikazu Ishii; Kiyoshi Horii, all of Tokyo, Japan

[73] Assignee: Nippon Telegraph and Telephone Corporation, Tokyo, Japan

[21] Appl. No.: 774,837

[22] Filed: Dec. 27, 1996

[30] Foreign Application Priority Data

Dec. 27, 1995 [JP] Japan .................................... 7-340345

[51] Int. Cl.⁶ .................................................. G01N 21/73
[52] U.S. Cl. .......................................... 356/316; 250/288
[58] Field of Search .......................... 356/316; 250/288; 219/121.48, 121.5, 121.51; 313/231.31

[56] References Cited

U.S. PATENT DOCUMENTS

| | | | |
|---|---|---|---|
| 4,266,113 | 5/1981 | Denton et al. | 219/121.51 |
| 4,551,609 | 11/1985 | Falk | 356/316 |
| 4,721,126 | 1/1988 | Horii . | |
| 4,818,916 | 4/1989 | Morrisroe | 356/316 |

FOREIGN PATENT DOCUMENTS

| | | |
|---|---|---|
| 0 335 448 A1 | 10/1989 | European Pat. Off. . |
| 0 397 468 A2 | 11/1990 | European Pat. Off. . |
| 04026099 | 1/1992 | Japan . |
| 2180957 | 4/1987 | United Kingdom . |

OTHER PUBLICATIONS

J.C. Eames et al., "Practical Design for an ICP Demountable Plasma Torch", 1369 Applied Spectroscopy 46 (1992), N. 11, pp. 1745–1746.

Thomas R. Smith et al., "A High–Pressure Inductively Coupled Plasma Torch", 1369 Applied Spectroscopy 41 (1987) May/Jun., No. 4, pp. 654–657.

*Primary Examiner*—F. L. Evans
*Attorney, Agent, or Firm*—Townsend and Townsend and Crew LLP

[57] ABSTRACT

In an elemental analysis method of analyzing a sample as an analysis target using atoms generated upon dissociation of the sample, a plasma is generated using a gas serving as a plasma source to be supplied in a torch having a conical cylinder thereof. A sample flow obtained by evaporating the sample using the gas as a carrier gas or a sample flow containing a component of the sample is supplied to the plasma. The sample flow or the plasma containing the sample flow is changed into a spiral flow, and the component of the sample is dissociated. The sample is analyzed in accordance with the state of an atom generated by dissociation of the component of the sample. An elemental analysis apparatus is also disclosed.

7 Claims, 5 Drawing Sheets

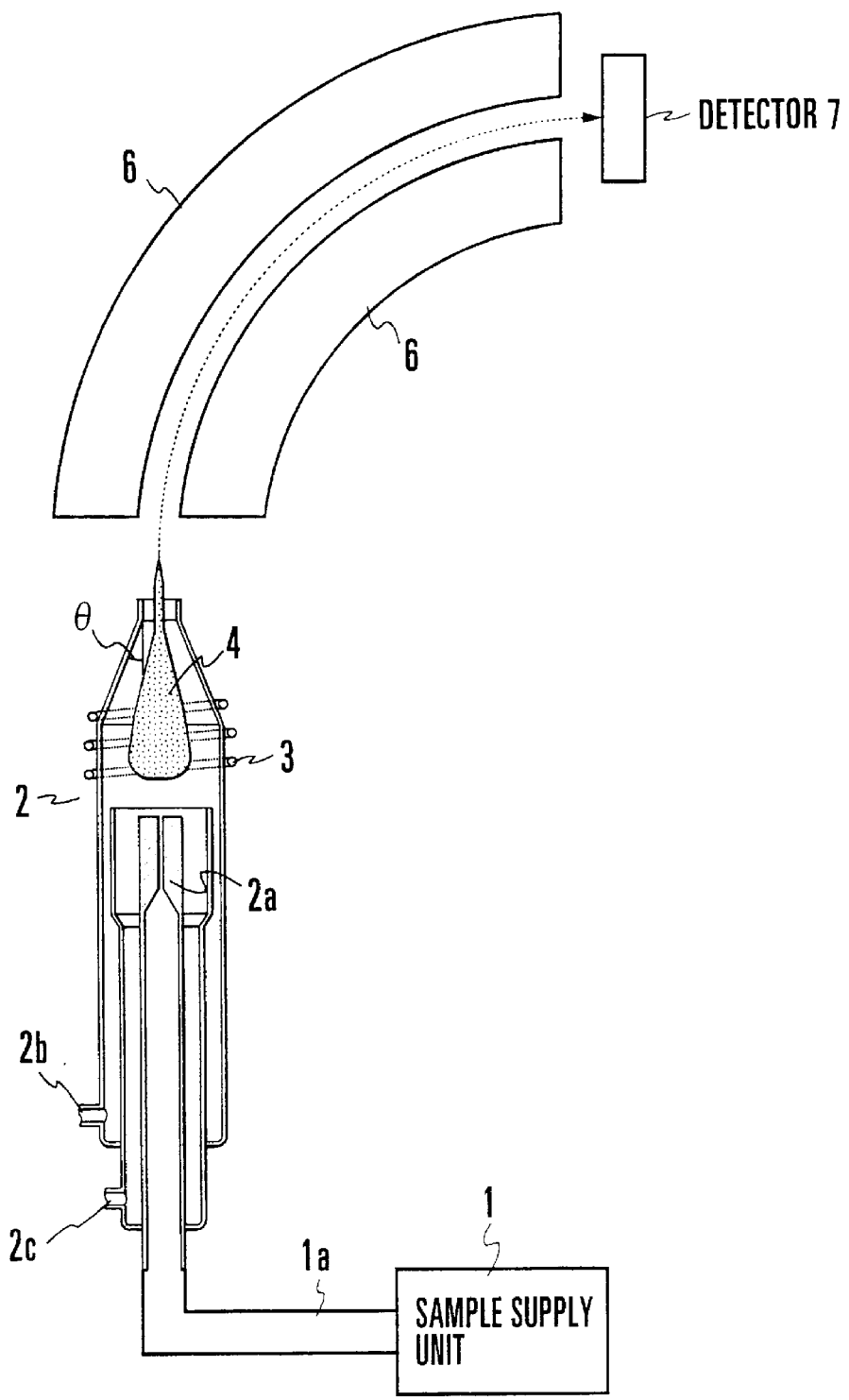
F I G. 2

ELEMENTAL ANALYSIS METHOD AND APPARATUS

BACKGROUND OF THE INVENTION

The present invention relates to an elemental analysis method and apparatus.

General analysis methods of elements contained in samples are atomic-emission spectroscopy, atomic absorption spectroscopy, mass spectroscopy, and the like. Among them all, RF inductively coupled plasma (ICP)-mass spectroscopy using an RF inductively coupled plasma torch is very popular because of its features excellent in sensitivity and accuracy. The RF inductively coupled plasma-mass spectroscopy has a higher detection limit than that of RF inductively coupled plasma-atomic emission spectroscopy by three or more orders of magnitude and can analyze the concentration of an element on the order of ppt or less.

A method of increasing the sensitivity in elemental analysis is to provide a higher-sensitivity detection system and a higher-efficiency sample supply system. Detection systems have been improved by employing a higher-sensitivity detection method and a high-transmittance detector. In an analysis method using an RF inductively coupled plasma torch, a detection method is changed from a method using a mass spectrometer to RF inductively coupled plasma-mass spectroscopy using a high-sensitivity plasma system spectrometer. This makes it possible to obtain a higher sensitivity than that of the RF inductively coupled plasma-atomic emission spectroscopy by three or more orders of magnitude. In the RF inductively coupled plasma-mass spectroscopy, a double focusing mass spectrometer is employed in place of a quadrupole mass spectrometer to increase the sensitivity, and an apparatus having a detection limit of ppq which is $\frac{1}{1000}$ of ppt is commercially available.

The efficiency of a sample supply system has been improved by the development of an ultrasonic nebulizer and a desolvating nebulizer. It is known that the sensitivity in use of such a nebulizer can increase that in use of an ordinary nebulizer by about one to two orders of magnitude.

Industry of high purity materials such as semiconductor materials necessitates the development of a higher-sensitivity analysis method and its improvement. Although the shape of a high-temperature flame depends on control of a sample flow, the sample flow is currently controlled by only its pressure and flow rate. The RF inductively coupled plasma-atomic emission spectroscopy and the RF inductively coupled plasma-mass spectroscopy will be taken as examples. Pressurized argon gas is simply passed through a pipe in a currently commercially available apparatus. Although pressure control using a reducing valve and flow control using a flowmeter are, of course, performed, the sample flow itself is not controlled. As a result, argon is passed through the pipe in a turbulent flow state. This turbulent flow causes a pulsating flow which then causes instability of a plasma flame. The plasma flame is observed to have fluctuations such that the flame instantaneously extincts and repeats the ON and OFF states due to the generation of the pulsating flow. The instability of this plasma flame appears as variations in emission intensity and ion intensity, resulting in degradation of the accuracy. In addition, an argon turbulent flow is dispersed at a torch portion, and a focused plasma flame cannot be obtained. For this reason, the commercially available apparatus employs a scheme for obtaining a focused plasma flame by using a plasma torch having a triple structure in which a sample flow is surrounded by a double gas flow. A satisfactorily focused plasma flame, however, cannot be obtained. Therefore, a high-sensitivity, high-accuracy elemental analysis cannot be performed.

SUMMARY OF THE INVENTION

The present invention has been made to solve the conventional problems described above, and has as its object to provide an elemental analysis method and apparatus capable of analyzing an element with a high sensitivity and a high accuracy.

In order to achieve the above object according to an aspect of the present invention, there is provided an elemental analysis method of analyzing a sample as an analysis target using atoms generated upon dissociation of the sample, comprising generating a plasma using a gas serving as a plasma source to be supplied in a torch having a conical cylinder thereof, supplying to the plasma a sample flow obtained by evaporating the sample using the gas as a carrier gas or a sample flow containing a component of the sample, reforming the sample flow or the plasma containing the sample flow into a spiral flow and dissociating the component of the sample, and analyzing the sample in accordance with a state of an atom generated by dissociation of the component of the sample.

According to another aspect of the present invention, there is provided an elemental analysis apparatus for analyzing a sample as an analysis target using atoms generated upon dissociation of the sample, comprising a torch having a coil for applying an RF power to an ambient atmosphere, a plasma chamber for generating a plasma using the RF power and dissociating the sample, and a conical cylinder at a given taper angle to emit the generated plasma, a sample supply unit for delivering a sample solution toward the plasma chamber, an auxiliary gas supply unit for delivering an auxiliary gas serving as a plasma source from a peripheral portion of the sample supply unit to the plasma chamber to evaporate the sample solution delivered from the sample supply unit, a main gas supply unit serving as a plasma source from a peripheral portion of the auxiliary gas supply unit to the plasma chamber to supply a main gas for cooling a wall surface of the torch, and a detector arranged at an emission destination of the plasma in the torch to detect a state of an atom of the sample dissociated by the plasma.

BRIEF DESCRIPTION OF THE DRAWINGS

FIG. 2 is a schematic view showing another elemental analysis apparatus according to the present invention;

DESCRIPTION OF THE PREFERRED EMBODIMENTS

Figure 1:
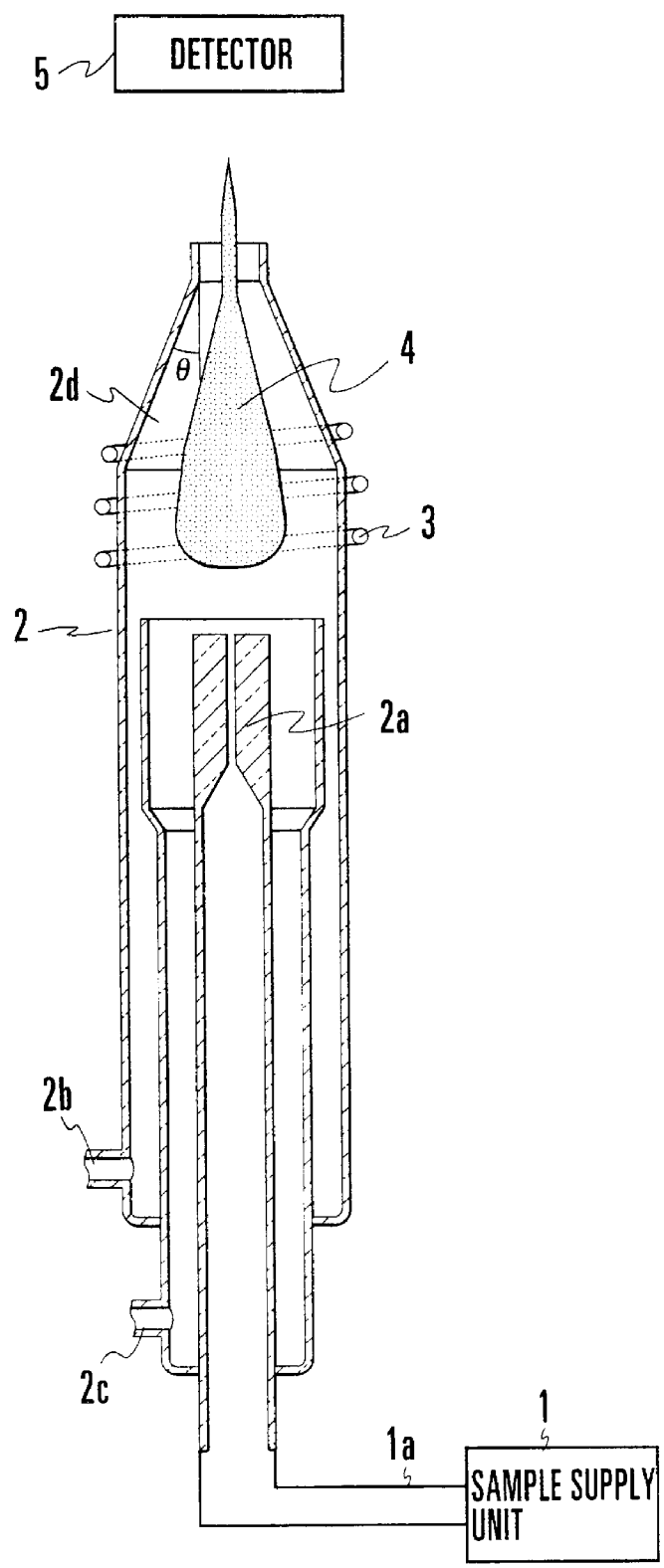
FIG. 1 is a schematic view showing an elemental analysis apparatus according to the present invention.

FIG. 1 shows the main part of an atomic absorption spectrochemical analysis apparatus using spiral flow ICP.

As shown in FIG. 1, a sample solution in a sample supply unit 1 is supplied to a tube 2a of a plasma torch 2 through a sample tube 1a.

This silica glass plasma torch 2 has a triple structure. Ar gas is supplied from a cooling gas system 2b and an auxiliary gas system 2c so as to surround the sample supply tube 2a.

A plasma chamber 2d of the plasma torch 2 has a conical cylinder. In addition, an RF addition cold coil 3 is wound on the plasma chamber 2d. When an RF power (27.12 MHz) is applied from the cold coil 3 to the plasma chamber 2d while Ar is kept supplied to the plasma chamber 2d, a plasma 4 is generated in the plasma chamber 2d.

Ar supplied from the cooling gas system 2b is consumed as a plasma source in the plasma chamber 2d while cooling the outer wall of the plasma torch 2.

Ar supplied from the auxiliary gas system 2c is supplied to push up the plasma 4 generated in the plasma chamber 2d so as not to drop the plasma 4 to the distal end portion of the sample supply tube 2a. In addition, this Ar gas is supplied from a portion near the distal end of the sample supply tube 2a, so that the sample solution is evaporated and the sample gas is supplied from the distal end of the sample supply tube 2a to the plasma chamber 2d.

The vapor of the sample solution is supplied to the plasma chamber 2d in which the plasma 4 is generated upon application of an RF power. The sample supplied to the plasma 4 is ionized by the plasma 4. The outer diameter of the plasma torch 2 is 20 mm, the diameter d of a nozzle at the distal end of the plasma torch 2 is 11 mm, and the taper angle θ of the torch portion is 13°.

The emission or absorption spectrum of the sample ionized in the plasma 4 is detected by a detector 5 to analyze the ions.

FIG. 2 shows the main part of a mass spectrometer using the ICP according to the present invention. In this mass spectroscopy, a sample ionized in a plasma chamber 2d of a plasma torch 2 and emitted from the plasma torch 2 is deflected in a magnetic field from a separator 6. The deflected ionized sample reaches a mass spectrometer 7 comprised of a Faraday cup and is detected by this mass spectrometer 7. In this mass spectrometer, the outer diameter of the plasma torch 2 is 20 mm, the diameter of a nozzle at the distal end of the plasma torch 2 is 11 mm, and the taper angle θ of the distal end portion is 13°.

Unlike in this embodiment, in a conventional plasma torch whose distal end is not tapered, supply ports of cooling and auxiliary gases are offset from the center, thus providing a structure with a certain rotating component. That is, a turbulent flow is generated in a conventional torch, but does not produce a satisfactorily focused plasma flame.

Even if the outlet port of a torch is simply tapered, a focused plasma flame cannot be obtained. This simply tapered outlet port increases a pressure loss and fails to assure a static pressure. Therefore, a gas tends not to flow and cannot be focused.

To the contrary, in this embodiment, the conical cylinder of the plasma torch 2 is tapered into a given shape (conical shape). When a gas is supplied, it becomes a spiral flow. The spiral flow produces a stable plasma flame upon application of an RF power to the spiral flow.

The given shape is obtained by setting the Reynolds number ($S_{Re}$) to −6 or less in the radial direction of the gas flow.

The Reynolds number $S_{Re}$ is defined as $S_{Re}=V_r R/\gamma_R$ where $V_R$ is the function $V_r=f(V_{za}, \theta)$ between the average axial velocity $V_{za}$ and the taper angle θ at the conical cylinder of the torch, and $\gamma_R$ is the kinematic viscosity. The diameter of the distal end portion of the torch is defined as d=2R.

A spiral flow is apparently generated when the Reynolds number is −6 or less. More specifically, when the diameter of the distal end portion of the torch is 0.1 to 100 mm, and the taper angle of the distal end portion of the torch falls within the range of 5° to 60°, a spiral flow is generated.

Figure 3:
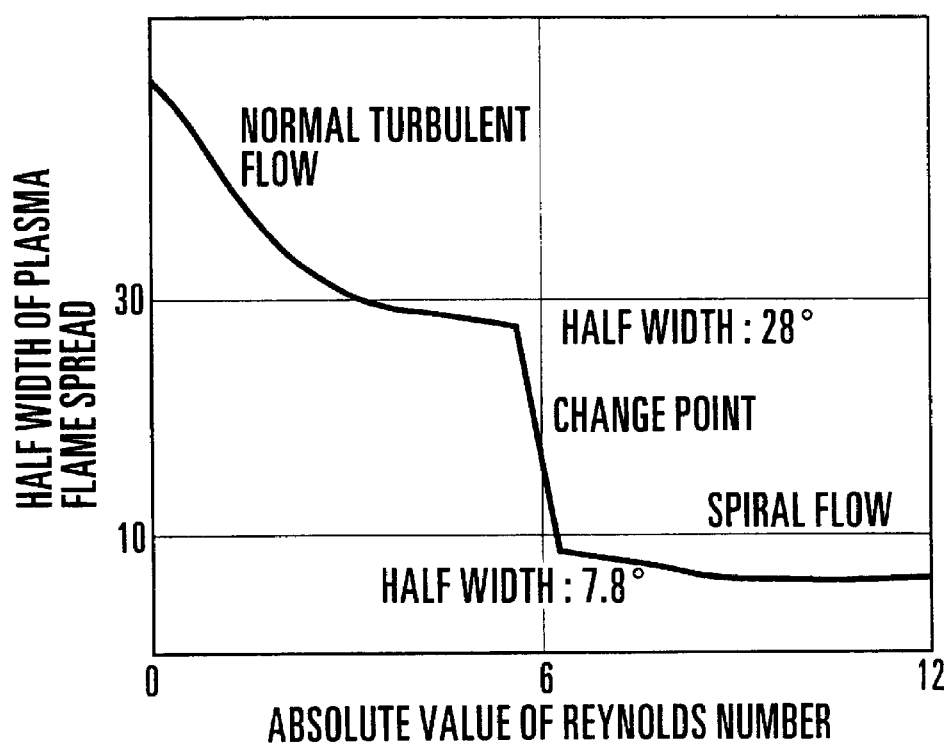
FIG. 3 is a graph showing the difference between a normal turbulent flow and a spiral flow in a torch of the present invention.

FIG. 3 shows the difference between a normal turbulent flow and the spiral flow obtained by the torch of this embodiment. The Reynolds numbers of the turbulent flow and the spiral flow for a swirl number of 0.3 are plotted along the abscissa of FIG. 3, and the half widths of the plasma flame spreads are plotted along the ordinate of FIG. 3.

As can be apparent from FIG. 3, the half width of the plasma flame spread abruptly decreases near |6| of the Reynolds number to obtain a spiral flow, thereby focusing the plasma flame.

As described above, the same sample supply amount is set for the conventional torch and the above-described spiral flow torch of the present invention, the concentrations of impurities, i.e., sample elements to be detected, except for Ar contained in the plasma flame are increased by a focused component.

When the diameter of an area where the focused plasma flame can be detected is much smaller than the outer diameter of the plasma flame, the above effect can be greatly enhanced. For example, when the diameter of the area where the plasma flame can be detected is set ½ the outer diameter of the plasma flame, the impurity concentration increases four times, so that the sensitivity increases four times. When the diameter of the area where the plasma flame can be detected is set ⅓ the outer diameter of the plasma flame, the impurity concentration becomes nine times. Therefore, the sensitivity becomes nine times accordingly, and the sensitivity increases by about one order of magnitude.

The spiral flow is as close as a laminar flow and is almost free from a pulsating flow. The spiral flow also has a strong directivity, so that a stable flame almost free from fluctuations can be obtained. For this reason, the impurity and plasma profiles can be obtained with good repeatability, and the repetition accuracy can be improved.

Figure 4:
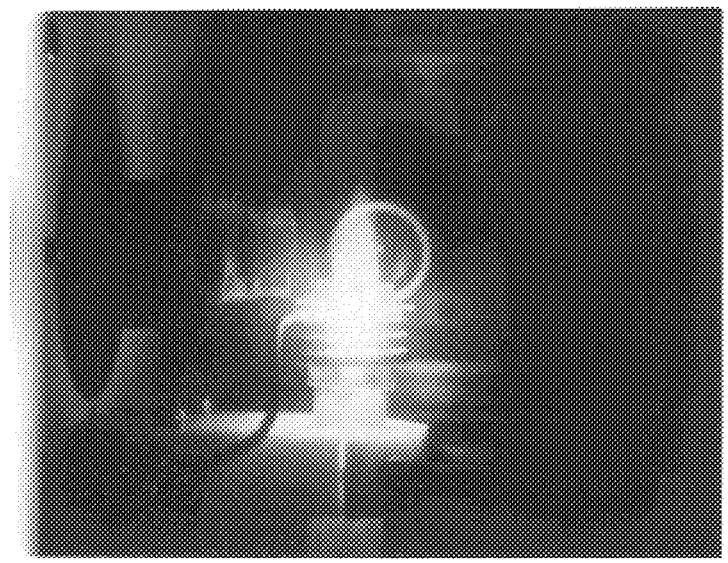
FIG. 4 is a view showing the actual state of a conventional plasma torch.
Figure 5:
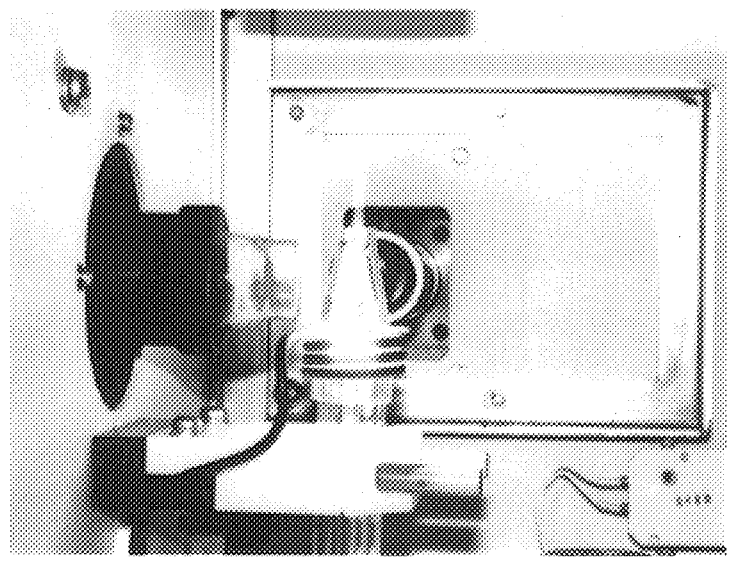
FIG. 5 is a view showing the actual state of the plasma torch of the present invention.

FIGS. 4 and 5 show the states of plasmas obtained by the conventional plasma torch and the plasma torch of the present invention, respectively.

A 27.12-MHz RF power having an output of 1 kW was applied to the plasma chamber of each torch, and a sample flow was supplied at a flow rate of 0.55 (l/min). Ar was supplied as a cooling gas at a flow rate of 15 (l/min), and Ar is supplied as auxiliary gas at a flow rate of 0.5 (l/min).

As shown in FIG. 4, a plasma flame is not focused in the conventional plasma torch. As shown in FIG. 5, however, a plasma flame is focused in the plasma torch of the present invention.

Consequently, in the elemental analysis apparatuses shown in FIGS. 1 and 2 and the elemental analysis method using such an apparatus, since the sample flow becomes a spiral flow in the plasma torch, the focused plasma flame can be obtained. As a result, an element contained in a sample in a very small amount can be analyzed with a high sensitivity.

As the central portion of the plasma flame of the spiral flow has a high flow velocity, the plasma flame does not almost interact with the tube wall of the torch. As shown in FIG. 5, the plasma flame will not directly contact the tube wall of the torch. The plasma flame does not melt the torch, and the analysis sensitivity and accuracy are not adversely affected by contamination caused by chemical reactions between the torch and the sample components.

Since a stable plasma flame almost free from fluctuations can be obtained according to the present invention, elemental analysis can be performed with a high accuracy.

For example, when a 10 ppm lanthanum solution was subjected to mass spectroscopy using a conventional plasma torch at a sample flow rate of 1.0 (l/min) under the conditions that an RF output having a frequency of 27.12 MHz was set to 1.4 kW, a cooling gas flow rate was set to 12.0 (l/min), and auxiliary gas flow rate was set to 0.5 (l/min), the intensity of $^{139}$La was counted as $7.4 \times 10^{10}$ in a Farady cup (detector) measurement.

To the contrary, under the same conditions as described above, in the analysis in the mass spectrometer (FIG. 2) using the plasma torch of the present invention, the intensity of $^{139}$La was counted as $1.6 \times 10^{11}$, thus improving the sensitivity to about twice that of the conventional analysis.

As the repeatability in 10 measurements, the relative standard deviation (RSD) in the analysis using the conventional plasma torch was 4.04%. However, in the analysis using the plasma torch of the present invention, the relative standard deviation was 1.04%, which greatly improved the accuracy. In addition, since the plasma flame is surrounded by the gases at the distal end portion of the torch, sensitivity and accuracy degradations caused by interference of components in the air can be prevented.

Figure 6:
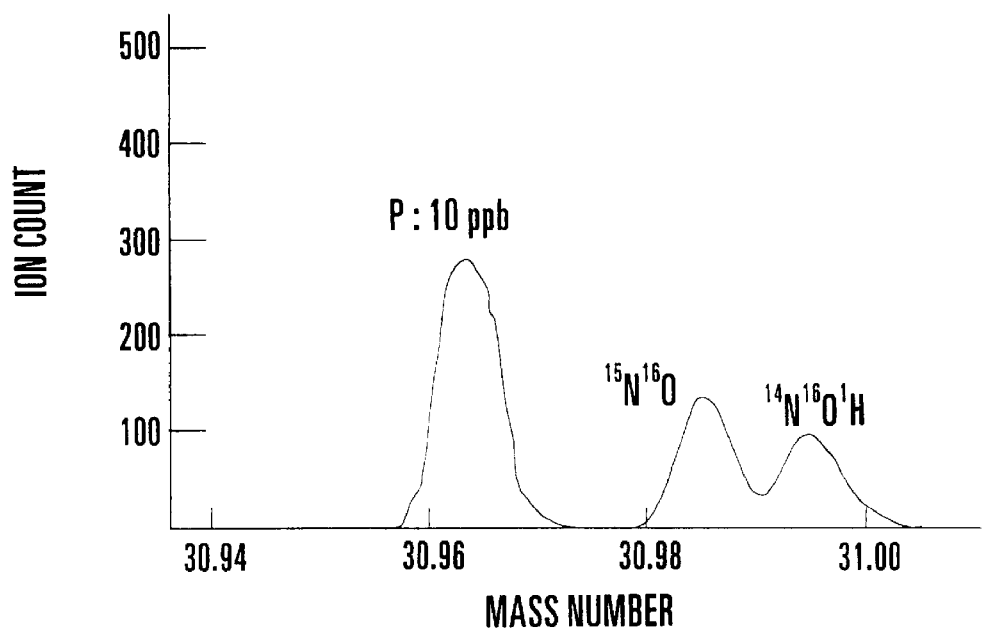
FIG. 6 is a graph showing a phosphorus analysis result using a mass spectrometer using the conventional torch.

A phosphorus analysis will be described below. FIG. 6 shows a phosphorus analysis result in a mass spectrometer using the conventional torch, while FIG. 7 shows a phosphorus analysis result in a mass spectrometer using the torch of the present invention.

The concentration of a phosphorus sample to be analyzed is 10 ppb, and the analysis resolution is set to 3,000 or more.

As shown in FIG. 6, in the mass spectroscopy of $^{31}$P using an ICP, $^{15}$N$^{16}$O and $^{14}$N$^{16}$O$^{1}$H are interference ions.

Figure 7:
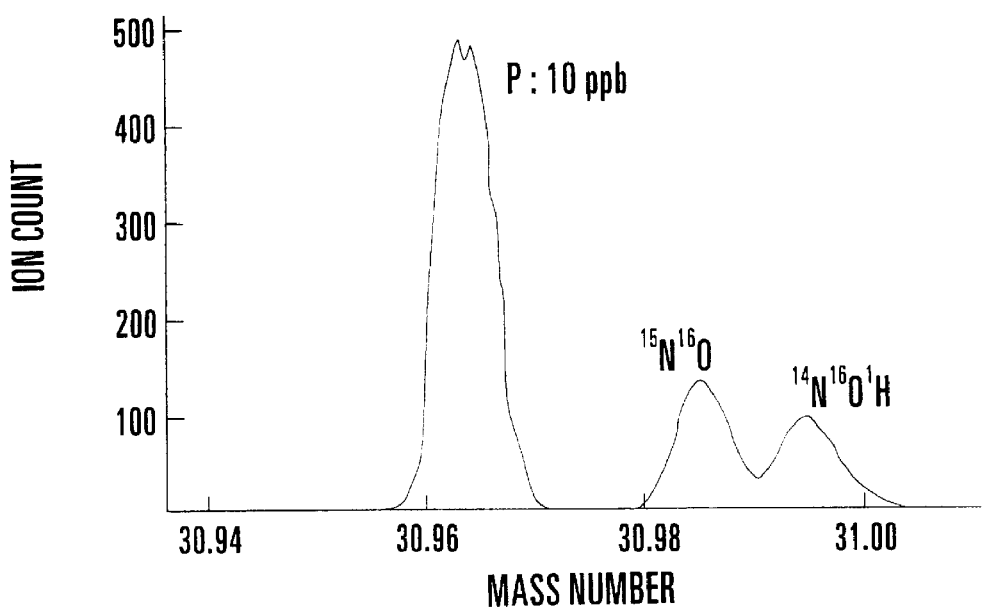
FIG. 7 is a graph showing a phosphorus analysis result using a mass spectrometer using the torch of the present invention.

As shown in FIG. 7, when the torch of the present invention is used, the $^{31}$P detection peak height becomes almost doubled. No changes occur in the detection peak heights of $^{15}$N$^{16}$O and $^{14}$N$^{16}$O$^{1}$H as interference ions. That is, as is apparent, the influence of the interference ions can be relatively halved by using the torch of the present invention.

As has been described above, the elemental analysis method and apparatus of the present invention use a torch in which the outlet port for emitting a generated plasma is conical cylinder with a given taper angle.

With this structure, a sample flow becomes a spiral flow to focus a plasma flame in an area of the torch where the plasma is generated.

According to the present invention, elemental analysis can be performed with a high sensitivity. At the same time, since a stable flame almost free from fluctuations can be obtained, elemental analysis can be performed with a high accuracy.

What is claimed is:

1. An elemental analysis method of analyzing a sample as an analysis target using atoms generated upon dissociation of the sample, comprising:

generating a plasma using a gas serving as a plasma source to be supplied in a torch having a conical cylindrical section thereof;

supplying to the plasma a sample flow obtained by evaporating the sample using the gas as a carrier gas or a sample flow containing a component of the sample;

reforming the sample flow or the plasma containing the sample flow into a spiral flow and dissociating the component of the sample; and analyzing the sample in accordance with a state of an atom generated by dissociation of the component of the sample.

2. An elemental analysis apparatus for analyzing a sample as an analysis target using atoms generated upon dissociation of the sample, comprising:

a torch having a coil for applying an RF power to an ambient atmosphere, a plasma chamber for generating a plasma using the RF power and dissociating the sample, and a conical cylindrical section with a given taper angle to emit the generated plasma;

a sample supply unit for delivering a sample solution toward said plasma chamber;

an auxiliary gas supply unit for delivering an auxiliary gas serving as a plasma source from a peripheral portion of said sample supply unit to said plasma chamber to evaporate the sample solution delivered from said sample supply unit;

a main gas supply unit for delivering a main gas serving as a plasma source from a peripheral portion of said torch to said plasma chamber to cool a wall surface of said torch; and a detector arranged at an emission destination of the plasma in said torch to detect a state of an atom of the sample dissociated by the plasma.

3. An apparatus according to claim 2, wherein said detector comprises photodetecting means for detecting optical characteristics of the atom in the plasma emitted from said torch.

4. An apparatus according to claim 2, wherein said detector comprises:

a separator disposed immediately after said torch; and an ion detector for detecting the atom emitted from said torch and passed through said separator.

5. An apparatus according to claim 2, wherein the taper angle is an angle defined such that the Reynolds number of said conical cylindrical section of said torch is not more than −6.

6. An apparatus according to claim 5, wherein said detector comprises photodetecting means for detecting optical characteristics of the atom in the plasma emitted from said torch.

7. An apparatus according to claim 5, wherein said detector comprises:

a separator disposed immediately after said torch; and an ion detector for detecting the atom emitted from said torch and passed through said separator.

* * * * *